US012711787B2

(12) United States Patent
Praljak et al.

(10) Patent No.: US 12,711,787 B2
(45) Date of Patent: Aug. 18, 2026

(54) CLASSIFICATION OF BLOOD CELLS

(71) Applicant: CASE WESTERN RESERVE UNIVERSITY, Cleveland, OH (US)

(72) Inventors: Niksa Praljak, Cleveland, OH (US); Shamreen Iram, Cleveland, OH (US); Utku Goreke, Cleveland, OH (US); Michael Hinczewski, Cleveland, OH (US); Ailis Hill, Cleveland, OH (US); Umut Gurkan, Cleveland, OH (US); Gundeep Singh, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 606 days.

(21) Appl. No.: 17/928,976

(22) PCT Filed: Jun. 3, 2021

(86) PCT No.: PCT/US2021/035707

§ 371 (c)(1),
(2) Date: Dec. 1, 2022

(87) PCT Pub. No.: WO2021/247868

PCT Pub. Date: Dec. 9, 2021

(65) Prior Publication Data

US 2023/0221239 A1 Jul. 13, 2023

Related U.S. Application Data

(60) Provisional application No. 63/185,781, filed on May 7, 2021, provisional application No. 63/034,252, filed on Jun. 3, 2020.

(51) Int. Cl.
*G06V 20/69* (2022.01)
*G01N 15/01* (2024.01)
(Continued)

(52) U.S. Cl.
CPC ....... *G06V 20/695* (2022.01); *G01N 15/1433* (2024.01); *G01N 33/49* (2013.01);
(Continued)

(58) Field of Classification Search
CPC ....... G06T 7/10–12; G06T 2207/20081; G06T 2207/20084; G06T 7/0012;
(Continued)

(56) References Cited

U.S. PATENT DOCUMENTS

| | | | |
|---|---|---|---|
| 10,684,207 | B2 | 6/2020 | Correia De Matos Nolasco Lamas et al. |
| 10,957,041 | B2 | 3/2021 | Yip et al. |

(Continued)

FOREIGN PATENT DOCUMENTS

| | | | |
|---|---|---|---|
| WO | 2017/210494 | A1 | 12/2017 |
| WO | 2019/178561 | A2 | 9/2019 |

(Continued)

OTHER PUBLICATIONS

Zhang, Xiaoqing, and Shuguang Zhao. "Blood cell image classification based on image segmentation preprocessing and CapsNet network model." Journal of Medical Imaging and Health Informatics 9.1 (2019): 159-166. (Year: 2019).*

(Continued)

*Primary Examiner* — Geoffrey E Summers
(74) *Attorney, Agent, or Firm* — Tarolli, Sundheim, Covell & Tummino LLP

(57) ABSTRACT

In a disclosed example, a computer-implemented method includes storing image data that includes an input image of a blood sample within a blood monitoring device. The method also includes generating, by a machine learning model, a segmentation mask that assigns pixels in the input image to one of a plurality of classes, which correlate to
(Continued)

respective known biophysical properties of blood cells. The method also includes extracting cell images from the input image based on the segmentation mask, in which each extracted cell image includes a respective cluster of the pixels assigned to a respective one of the plurality of classes.

21 Claims, 11 Drawing Sheets

(51) Int. Cl.

| | |
|---|---|
| ***G01N 15/02*** | (2024.01) |
| ***G01N 15/14*** | (2024.01) |
| ***G01N 15/1433*** | (2024.01) |
| ***G01N 33/49*** | (2006.01) |
| ***G06T 7/00*** | (2017.01) |
| ***G06T 7/11*** | (2017.01) |
| ***G06V 10/25*** | (2022.01) |
| ***G06V 10/26*** | (2022.01) |
| ***G06V 10/764*** | (2022.01) |
| ***G06V 10/82*** | (2022.01) |

(52) U.S. Cl.
CPC .............. *G06T 7/0012* (2013.01); *G06T 7/11* (2017.01); *G06V 10/25* (2022.01); *G06V 10/26* (2022.01); *G06V 10/764* (2022.01); *G06V 10/82* (2022.01); *G06V 20/698* (2022.01); *G01N 2015/012* (2024.01); *G01N 2015/0294* (2013.01); *G01N 2015/1486* (2013.01); *G01N 2015/1495* (2013.01); *G06T 2207/20084* (2013.01); *G06T 2207/30024* (2013.01); *G06T 2207/30242* (2013.01); *G06V 2201/03* (2022.01)

(58) Field of Classification Search
CPC . G06T 2207/30024; G06T 2207/30104; G06T 2207/30242; G06V 20/695; G06V 20/698; G06V 10/454; G06V 10/82; G06V 10/25; G06V 10/26; G06V 10/764; G06V 2201/03; G01N 2015/012; G01N 15/1433; G01N 2015/0294; G01N 2015/1486; G01N 2015/1495; G01N 33/49
See application file for complete search history.

(56) References Cited

U.S. PATENT DOCUMENTS

| | | | |
|---|---|---|---|
| 2017/0227495 | A1* | 8/2017 | Gurkan ............ G01N 27/44791 |
| 2018/0217043 | A1 | 8/2018 | Correia De Matos Nolasco Lamas et al. |
| 2019/0042826 | A1 | 2/2019 | Chang et al. |
| 2020/0152326 | A1 | 5/2020 | Sanchez-Martin et al. |
| 2020/0258223 | A1 | 8/2020 | Yip et al. |
| 2021/0216745 | A1* | 7/2021 | Gildenblat ............ G06F 18/217 |

FOREIGN PATENT DOCUMENTS

| | | | |
|---|---|---|---|
| WO | 2019/241443 | A1 | 12/2019 |
| WO | 2020/028313 | A1 | 2/2020 |

OTHER PUBLICATIONS

Xu, Mengjia, et al. "A deep convolutional neural network for classification of red blood cells in sickle cell anemia." PLOS computational biology 13.10 (2017): e1005746. (Year: 2017).*

Xia, Tiancheng, et al. "Automated blood cell detection and counting via deep learning for microfluidic point-of-care medical devices." IOP conference series: materials science and engineering. vol. 646. No. 1. IOP Publishing, 2019. (Year: 2019).*

Kajánek, František, and Ivan Cimrák. "Evaluation of detection of red blood cells using convolutional neural networks." 2019 International Conference on Information and Digital Technologies (IDT). IEEE, 2019. (Year: 2019).*

Hortinela, Carlos C., et al. "Identification of abnormal red blood cells and diagnosing specific types of anemia using image processing and support vector machine." 2019 IEEE 11th Intl. Conf. on HNICEM. IEEE, 2019. (Year: 2019).*

De Haan, Kevin, et al. "Automated screening of sickle cells using a smartphone-based microscope and deep learning." NPJ digital medicine 3.1 (2020): 76. (Year: 2020).*

Dhieb, Najmeddine, et al. "An automated blood cells counting and classification framework using mask R-CNN deep learning model." 2019 31st international conference on microelectronics (ICM). IEEE, 2019. (Year: 2019).*

Razzak, Muhammad Imran, and Saeeda Naz. "Microscopic Blood Smear Segmentation and Classification Using Deep Contour Aware CNN and Extreme Machine Learning." 2017 IEEE Conference on Computer Vision and Pattern Recognition Workshops (CVPRW). IEEE, 2017. (Year: 2017).*

Triscott, Mathew I. A Simple Microfluidic Device for Automated, High-Throughput Measurement Of Morphology of Stored Red Blood Cells. MS thesis. Tulane University, 2013. (Year: 2013).*

Ronneberger, Olaf, Philipp Fischer, and Thomas Brox. "U-Net: Convolutional Networks for Biomedical Image Segmentation." International Conference on Medical Image Computing and Computer-Assisted Intervention. Springer, Cham, 2015. (Year: 2015).*

Sabour, Sara, Nicholas Frosst, and Geoffrey E. Hinton. "Dynamic routing between capsules." Advances in neural information processing systems 30 (2017). (Year: 2017).*

Qiu, Wei, et al. "Multi-label Detection and Classification of Red Blood Cells in Microscopic Images." arXiv preprint arXiv: 1910. 02672v2 (2019). (Year: 2019).*

European Application No. 21819008.0, Extended Search Report dared Apr. 25, 2024.

Das Pradeep Kumar et al: "A Review of Automated Methods for the Detection of Sickle Cell Disease", IEEE Reviews in Biomedical Engineering, IEEE, USA, vol. 13, May 17, 2019 (May 17, 2019), pp. 309-324.

Zhang Mo et al: "RBC Semantic Segmentation for Sickle Cell Disease Based on Deformable U-Net", Sep. 13, 2018 (Sep. 13, 2018), Medical Image Computing and Computer Assisted Intervention—MICCAI 2018; [Lecture Notes in Computer Science; Lect.Notes Computer], Springer International Publishing, Cham, pp. 695-702.

Applicant: Case Western Reserve University; International Application No. PCT/US2021/035707; PCT International Search Report dated Sep. 24, 2021; 3 pgs.

* cited by examiner

Phase II: Classifier Network inserting new fully connected
classification layer
for our 3 category data set upper layers: trained to
recognize general image
features, i.e. edges, textures ResNet-50 lower layers: trained to
recognize higher level
image-specific features removing old 1000
category fully connected
classification layer

CLASSIFICATION OF BLOOD CELLS

RELATED APPLICATIONS

This application claims the benefit of U.S. Provisional Appln. Ser. No. 63/034,252, filed Jun. 3, 2020, and U.S. Provisional Appln. Ser. No. 63/185,781, filed May 7, 2021, the subject matter of which are incorporated by reference herein their entirety.

GOVERNMENT FUNDING

This invention was made with government support under HL133574, TR002548, and HL152643, awarded by the National Institutes of Health; and U.S. Pat. Nos. 1,552,782 and 1,651,560 awarded by the National Science Foundation. The government has certain rights in the invention.

TECHNICAL FIELD

This disclosure relates to systems and methods that employ machine learning to classify biophysical properties of cells, such as blood cells including sickle red blood cells (sRBCs).

BACKGROUND

Sickle cell disease (SCD) affects over 100,000 Americans and more than 4 million genetically predisposed individuals worldwide. The affected demographic commonly draws on ancestral lineage from parts of Africa and India. The most common form of SCD is caused by a single mutation in the β globin gene, leading to the expression of an abnormal form of hemoglobin, HbS, in red blood cells (RBCs).

Although SCD originates from a single deficit gene, there are many observed clinical sub-phenotypes associated with the disease. They are not mutually exclusive and some of the associated complications are seen to cluster together, suggesting independent genetic modifiers as their epidemiological underpinnings. These sub-phenotypes are associated with different acute and/or chronic complications. Common acute complications include pain crises, acute chest syndrome, stroke and hepatic or splenic sequestration. More long term effects include chronic organ damage of the lungs, bones, heart, kidneys, brain, and reproductive organs. The resultant heterogeneity among SCD patients belonging to different disease sub-phenotypes underlies the need for new methodologies to allow intensive patient specific evaluation and management in outpatient, inpatient and emergency department settings. SCD also requires early diagnosis after birth and constant clinical monitoring through the life-span of the patient, the absence of which leaves them prone to reduced quality of life and premature mortality.

The underlying biophysics of SCD hinges on associated complex dynamical phenomena playing out in the vascular flow environment. Mutated hemoglobin molecules expressed in affected sickle RBCs (sRBCs) have a tendency to polymerize in oxygen starved environments, forming long chains which distort the cell profile. The damaged cell membrane displays morphological sickling (distortion into a crescent shape) which dislocates the membrane molecules and leads to a stiffer membrane scaffolding. Consequently, sRBCs are more adhesive and less deformable than healthy RBCs. This increased membrane rigidity, along with altered adhesion characteristics that heighten interactions with the endothelium and plasma, directly give rise to SCD's key manifestation: recurring, painful vaso-occlusive crisis events triggered by sRBC aggregation and blood vessel clogging. The problem thus lends itself very naturally towards exploration in a microfluidic or adhesion assay setup. Microfluidic platforms used for evaluation of sRBC adhesion dynamics have the advantage of being able to directly use clinical whole blood taken from SCD patients. This is a versatile laboratory setup that allows one to mimic the complex vascular environment, and realistically explore the multiple, interconnected factors at play. These devices are thus good candidate tools for batch quantitative analyses of the mechanisms occurring in micro-vasculature prior to and during crises, as well as for testing intervention mechanisms. Manual quantification of images obtained using such microfluidic platforms is a rigorous, time consuming process and inherently reliant on skilled personnel. This makes it unsuitable for high throughput, operationally lightweight, easily replicable studies. Accordingly, there is a need for reliable, automated image analysis.

SUMMARY

This disclosure provides systems and methods that employ machine learning to classify sickle red blood cells (sRBCs).

In an example, a computer-implemented method includes storing image data that includes an input image of a blood sample within a blood monitoring device. The method also includes generating, by a machine learning model, a segmentation mask that assigns pixels in the input image to one of a plurality of classes, which correlate to respective known biophysical properties of blood cells. The method also includes extracting cell images from the input image based on the segmentation mask, in which each extracted cell image includes a respective cluster of the pixels assigned to a respective one of the plurality of classes.

In another example, a system includes a processor and one or more non-transitory machine readable media to store instructions and data. The data includes an image of a blood sample. The processor is configured to access the media and execute the instructions. The instructions include a machine learning model trained to generate a segmentation mask that assigns pixels in the image to one of a plurality of classes that correlate to respective known biophysical properties of blood cells. The instructions also include extraction code programmed to extract cell images from the input image based on the segmentation mask, in which each extracted cell image includes a respective cluster of the pixels assigned to a respective one of the plurality of classes.

In another example, one or more non-transitory machine readable media have instructions, executable by a processor to perform a method. The method can include retrieving image data that includes an input image of a blood sample. The method also includes using a first neural network to generate a segmentation mask that assigns each pixel in the image to a respective class of a plurality of classes that correlate to respective known biophysical properties. The method also includes generating cell images mages from the input image based on the segmentation mask in which each cell image includes a respective cluster of the pixels assigned to a respective one of the plurality of classes. The method also includes providing the input image set to a second neural network to classify respective objects in the input image set as corresponding to one or more subclasses of the respective class.

DETAILED DESCRIPTION

This disclosure provides systems and methods that employ machine learning to classify sickle red blood cells (sRBCs). The approach utilizes an automated, machine-learning-based framework to analyze assay images according to a standardized and reproducible automated image analysis workflow, which eliminates the need for user input and is capable of handling large amounts of data. The workflow implements a classification scheme to sort the sRBCs on the basis of biophysical properties that arise with progressive sickle hemoglobin, HbS, polymerization and sickling-features which strongly correlate with changes to the sRBC's bio-mechanical properties.

In an example, machine readable instructions are programmed to implement one or more (e.g., two) convolutional neural networks in tandem to perform segmentation/detection and classification of cells or other objects into respective subtypes. The systems and methods outline a processing pipeline that may be used as a high-throughput tool with detection, tracking, and counting capabilities that could be harnessed to assess visual bio-markers of disease severity. Thus, the systems and methods disclosed herein are suitable for integration into comprehensive monitoring and diagnostic platforms designed for patient specific clinical interventions—a key component of emerging targeted and curative therapies.

In one example, the systems and methods disclosed herein may be implemented in conjunction with the SCD Biochip, which is a customizable, in-vitro adhesion assay in which the microchannels can be functionalized with various endothelial proteins, and integrated with a programmable syringe pump unit that can implement physiologically relevant flow conditions. The analysis of the data from clinical whole blood samples injected into the SCD Biochip and similar experimental approaches has been challenging, with a major bottleneck being manual counting and categorization of cells from complex phase contrast or bright field microscopic images. The SCD Biochip may be used in a context that closely mimics the micro-vasculature in vivo, with cells from whole blood adhering to endothelial proteins under flow conditions. The workflow described herein thus is highly suitable for integration into comprehensive monitoring and diagnostic platforms, which may include the SCD Biochip, designed for patient specific clinical interventions a key component of emerging targeted and curative therapies.

In examples disclosed herein, the systems and methods are described in the context of analyzing and classifying subtypes of sRBCs. However, the systems and methods comprising the processing pipeline described herein are not limited to analysis of sRBC images alone, and may be translated for application to other classification problems, for biological as well as non-biological objects.

Figure 1:
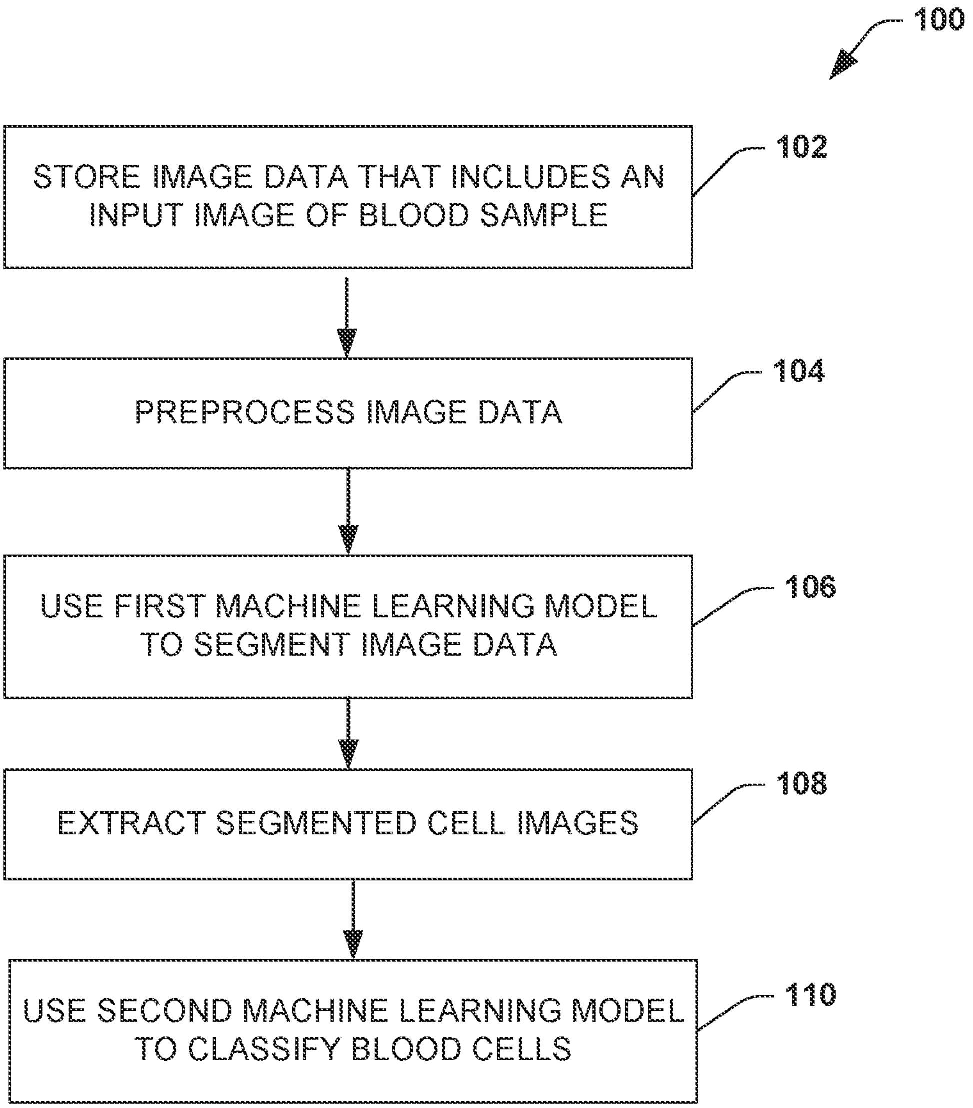
FIG. 1 is a flow diagram depicting an example of a method for classifying objects.

FIG. 1 is a flow diagram depicting an example of a method 100 that may be implemented for classifying objects. The method can be implemented as program code or modules (e.g., machine readable instructions), which are executable by one or more processors to perform the method 100. The instructions can be stored locally on a computing device that executes the instructions to run the code, or the instructions can be stored and/or executed by remote computing device (e.g., in a computing cloud, web-based or other networked architecture).

The method begins at 102 in which image data is stored in memory. The image data along with executable instructions may be stored in one or more non-transitory storage media, such as non-volatile data storage (e.g., a hard disk drive, a solid-state drive, flash memory, etc.). It will be appreciated that the storage medium may include a single discrete article or multiple articles interconnected to allow for data transfer among them, for example, via an associated bus or a local or wide-area network connection.

For example, the image data includes one or more images of a fluid sample within a device having at least one adhesion region adapted to adhere to cells of interest within the fluid sample. In one example, the device is a microfluidic device having a housing that includes at least one microchannel that defines one or more cell adhesion regions. Each respective cell adhesion regions include at least one capturing agent configured to adhere or capture to a cell of interest in a fluid sample when the fluid sample containing the cells is passed through the at least one microchannel.

As a further example, the fluid sample includes blood and the image data thus includes one or more images of the blood sample within an adhesion region of a microchannel of a microfluidic device, such as the SCD Biochip. Other microfluidic devices can be used in other examples. In an example, the blood sample is expected to include sickle red blood cells (sRBCs). The blood sample being imaged may also include a variety of other objects, which may be classified objects (e.g., classified by one more machine learning models as described herein) or unclassified objects. To facilitate imaging and analysis, the sRBCs may be adhered to an adhesion region of the microfluidic device.

As one example, the microfluidic device is implemented as an SBC Biochip fabricated by lamination of a polymethylmethacrylate (PMMA) plate, custom laser-cut double-sided adhesive film which has a thickness of about 50 μm (3M, Two Harbors, MN) and an UltraStick adhesion glass slide (e.g., commercially available from VWR International, LLC of Radnor, Pennsylvania). The image data stored at 102 may thus include one or more images of a volume of a blood sample that is perfused into the microchannels functionalized with bioaffinity ligands, such as laminin (e.g., available from Sigma-Aldrich of St. Louis, MO). Laminin is a sub-endothelial protein with preferential adherence to sRBCs over healthy RBCs. As a result, using laminin (or another type of similar functionalization agent) to define the adherence region allows the image analysis to focus on sRBC characterization. Other capturing agents can be used depending on the cells of interest. For example, when the fluid sample is synovial fluid, the cells of interest can be white blood cells (WBCs). As a further example, the microfluidic device can be implemented according to the disclosure in any of International Application No. PCT/US2018/022888, filed on 16 Mar. 2018, International Application No. PCT/US2020/058272, filed on October 2020, and International Application No. PCT/US2020/060227 filed 12 Nov. 2020, each of which is incorporated herein by reference.

As a further example, the image data (stored at 102) may be collected of the blood sample contained in a microfluidic device (e.g., SCD BioChip) using the following protocol. Shear stress was kept at approximately 0.1 Pa, mimicking the average physiological levels in post-capillary venules. After the non-adherent cells were removed by rinsing the microchannels, microfluidic images were taken by a microscope (e.g., Olympus IX83 inverted motorized microscope configured with a 10×/0.25 long working distance objective lens). For example, the images are acquired as a series of mosaic images that are stitched together into a montage image (e.g., by Olympus CellSense live-cell imaging and analysis software coupled with a Qlmaging CCD microscopy camera) to form the input image of the sample, which is stored as the image data (at 102).

In this and other examples disclosed herein, the objects in the images to be classified include blood cells including WBCs, RBCs and, in particular, sRBCs. The methods disclosed herein are programmed to analyze respective images and identify selected image properties of blood cells within such images that have been determined to correlate to respective biophysical properties of the blood cells. That is, certain image properties (e.g., dimples, edges and the like) are used as proxies for biophysical properties of sRBCs because such image properties have been determined to correlate to respective biophysical properties of sRBCs.

Other possible image properties that could correlate to biophysical aspects include the grayscale shade of the cell relative to the background, the overall size of the cell, the degree of circularity/ellipticity, the smoothness of the cell boundary (i.e., the presence or absence of cellular protrusions). Other image properties or combinations of properties can be used in other examples. Biophysical properties of RBCs, specifically sRBCs adhered to an adhesion region of a microfluidic device, can include deformability, morphology and adhesive strength. As disclosed herein, for example, the method 100 can be programmed to classify sRBCs into multiple sub-classes (or categories) having distinct biophysical properties, including deformable and non-deformable sRBCs, based on correlated image properties. The cells corresponding to the deformable class retain the RBC bi-concave detail, while the non-deformable sRBCs lose the bi-concave feature. While the bi-concave feature for deformable sRBCs is visible to the naked eye, including when adhered to a channel wall of the microfluidic device, in many cases detecting deformable sRBCs via human analysis can be complicated and inconsistent. In addition to their deformability properties, these two classes of cells are also distinguishable in terms of their adhesion strength to endothelial and sub-endothelial proteins under fluid forces, making them potentially significant for understanding the biophysics of vaso-occlusive crises.

Figure 2:
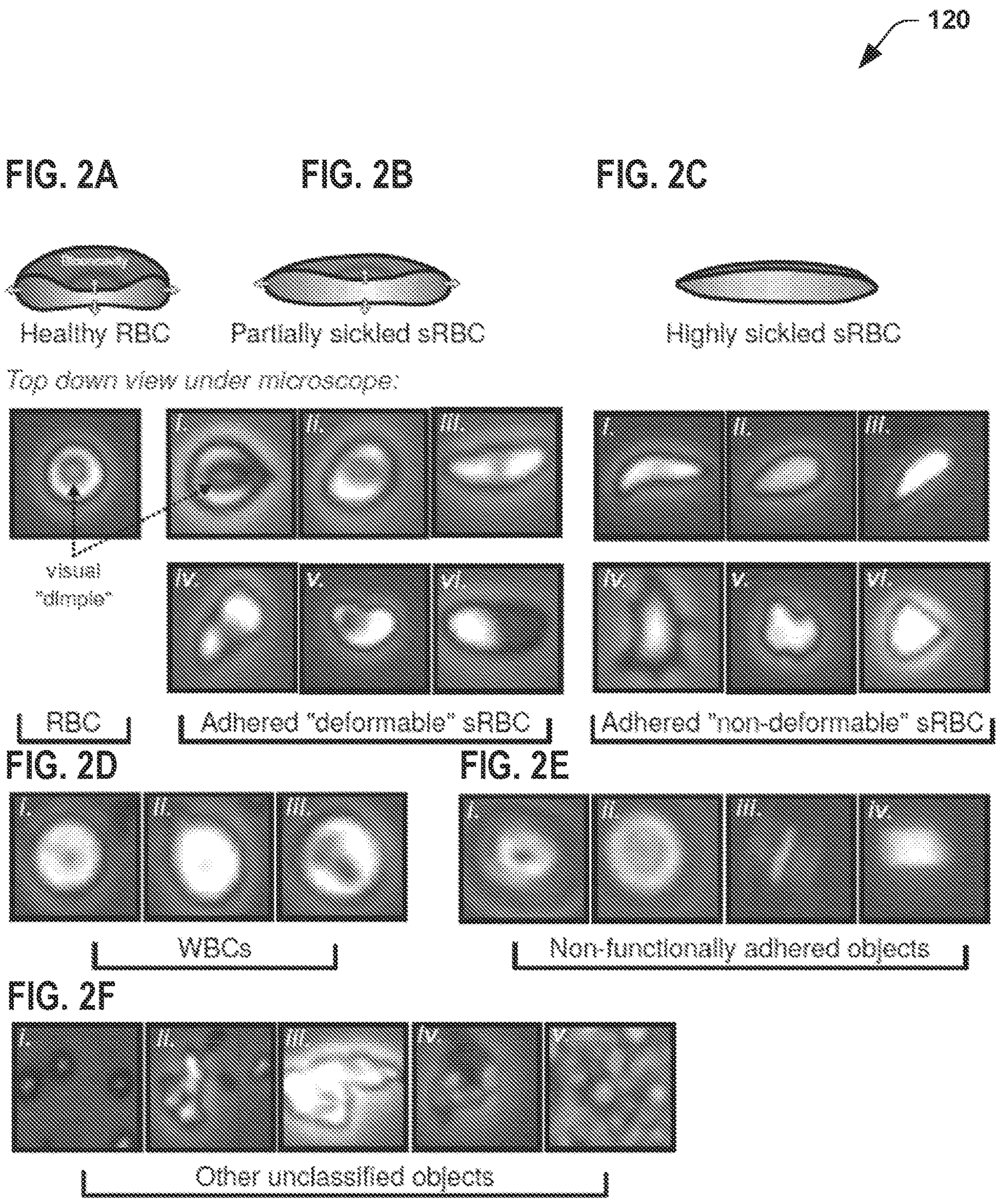
FIGS. 2A, 2B, 2C, 2D, 2E and 2F depict graphical representations of different categories of objects.

As an example, FIG. 2 depicts examples of object categories into which the systems and methods may classify objects within one or more images (in the image data stored in memory at 102). FIG. 2A illustrates a healthy RBC. Healthy RBCs are easily identifiable from their circular shape with an apparent dimple arising from a top-down view of the bi-concave cell profile (e.g., under microscope).

SCD pathogenesis (progressive stages of HbS polymerization) causes diseased RBCs to undergo deformation of their cell profile, going from a round to a more elongated, spindle-like shape. Simultaneously, the bi-concavity starts distending outwards. FIG. 2B illustrates partially sickled sRBCs at increasing stages of sickling. The bi-concavity distends out to give a shallower dimple, and elongation in profile. This is the category that is identified herein as a deformable sRBC. FIG. 2C illustrates examples of highly sickled sRBCs in which the dimple has completely disappeared and the shape is highly elongated. Cells at this stage of advanced disease progression, accelerated in hypoxic environments, become highly needle-like in shape, and can completely lose their concavity. The highly sickled sRBCs thus are classified herein into a non-deformable category of sRBC. Factors like local flow patterns, applied shear forces, and oxygen levels in the environment give rise to various shapes (teardrop, star-like, amorphous) for different sRBCs. These two categories of adhered sRBC (e.g., deformable and non-deformable) also correlate with biomechanical characteristics of the cell membrane, and we will label them by their membrane deformability, as described herein.

In addition to RBCs, blood sample may also include white blood cells (WBCs), such as shown in FIG. 2D. As mentioned, the functionalization protein laminin has known sRBC binding capabilities, and shows little WBC adhesion. The images thus exhibit WBCs with far less frequency relative to sRBCs. The WBCs that do adhere can be identified (and categorized as such) from a regular, round shape and smooth appearance, with varying degrees of internal detail.

As a further example, the focal plane of the microscope objective, which acquires the images that provide the image data 102, may be set to the protein-functionalized bottom of the channel. Objects adhered to this surface are thus in focus and thus visible in the images. Due to the finite height of the channel, non-specifically adhered objects outside the focal plane may be stuck to the PMMA coverslip on the channel or flow by in motion show up as out-of-focus objects in the images. Such objects exhibit characteristic diffraction rings or a blurred appearance as shown in FIG. 2E. Various unclassified categories of other objects can also appear in the images. As shown in FIG. 2F, examples include platelet clusters, cellular debris from lysed cells, and dirt/dust. Along with these objects, the background itself can show considerable variation in luminosity and level of detail, depending on the sample and experimenter.

Returning to FIG. 1, at 104, the method includes preprocessing image data. The image preprocessing can include loading the image data from memory (e.g., stored at 102) which will evenly crop the original whole channel image into smaller tiles and resize respective tiles so that they fit into the input layer for of a neural network model, as disclosed herein. The image data can be provided automatically from a process (e.g., through an API) or it can be selected from memory in response to a user input. The preprocessing at 104 can include cropping the input image (e.g., a large whole channel image) into smaller image tiles. The cropped size can vary depending on the size requirements for the input layer of the machine learning model (e.g., shown at 106). As one example, an input image having a pixel size 15000×5250×3, can be resized at 104 to a plurality of smaller image tiles having a size of 224×224×3. The preprocessing can also that each image contains three channels. In some examples, which may depend on the experimental conditions with the microscope, grayscale images having different numbers of channels (e.g., both one and three channels) can be accommodated. For instance, if a whole microchannel image has one channel, the preprocessing can be programmed to copy and concatenate the first channel so as to output a three channel depth gray scale image.

At 106, the method includes using a first machine learning model to segment image data. For example, the preprocessed input image can be provided to a pre-trained neural network model. For example, the first machine learning model is pre-trained to segment each image tile (e.g., from the respective image tiles provided at 104) by classifying individual pixels and providing respective output images of cells of interest based on respective trained categories that correlate to biophysical properties of cells. In an example, the machine learning model is configured to detect and distinguish sickle RBCs adhered to the functionalized channel with endothelial proteins relative to other objects (e.g., other RBCs, WBCs or other non-blood cell objects) provided in the input image tiles. The machine learning model can also output a count to identify a number objects classified in each category based on the segmented respective output images of cells of interest provided at 106.

In the following examples described herein, the first machine learning model is an artificial neural network and, in particular, a convolutional neural network configured to perform semantic segmentation of each input image. In other examples, the machine learning model may one or more of a decision tree, a support vector machine, a clustering process, a Bayesian network, a reinforcement learning model, naïve Bayes classification, a genetic algorithm, a rule-based model, a self-organized map, and an ensemble method, such as a random forest classifier or a gradient boosting decision tree). The training process of a given model will vary with its implementation, but training generally involves a statistical aggregation of training data into one or more parameters associated with the output classes. In some examples, the machine learning model that analyzes the image is described as a first model because the method 100 includes multiple phases of deep learning, in which the first phase includes a machine learning model that implements segmentation and detection of objects that drives another phase of deep learning that includes another machine learning model to implement object classification.

As a further example, the machine learning model utilized at 106 implements a convolutional neural network (CNN) model to classify pixels in the image according to a respective class of sRBCs. For example, the CNN model implements an architecture (e.g., a U-net architecture—see, e.g., FIG. 4) programmed to downsample the input image to generate feature vectors and to upsample based on the feature vectors to generate a segmentation mask to classify pixels for detecting cell objects. As used herein, a segmentation mask refers to a representation of the input image in which each pixel thereof is assigned (e.g., annotated or labeled) to belong to a respective class. The respective class may be selected from a group (or set) of classes that can be represented in a given multi-class segmentation mask. In one example, the classes include deformable sRCBs, non-deformable sRBCs, non-functionally adhered objects/other and background. In another example, the CNN model may implement a binary classification of pixels into respective combined classes, such as including sRBCs and non-sRBCs or adhered sRBCs and non-adhered sRBCs. The CNN model thus may generate the segmentation mask to specify cell objects (sRBCs) in the input image, which have been segmented from clusters of pixels in the input image based on the assigned class of the pixels.

At 108, the method 100 includes extracting a set of cell images from the input image based on the segmentation at 106. Each cell image includes a respective cluster of pixels assigned to the respective class (e.g., a combined class of adhered sRBCs). For example, the segmentation of cell images from the segmentation mask at 106 may be implemented by clustering pixels in connected neighborhoods of the same pixel class in the image according to the respective class label. The extraction can compute centroids for each segmented cell (e.g., each segmented sRBC adhered to the functionalized wall with endothelial proteins) based on the image tiles and masks provided at 106. Bounding boxes (e.g., spatial coordinates) around each identified centroid may be determined so that each cell image in the image set is generated based on pixels residing within a respective bounding box. Other areas in the image may be ignored and/or discarded so as not be processed at 110.

At 110, the method includes classifying respective objects provided in each of the extracted cell image provided at 108. For example, the classification can be implemented by a second machine learning model pre-trained to classify respective blood cells in each cell image as one of a number of blood cell categories, such as a deformable sRBC, a non-deformable sRBC or a non-sRBC. For example, the second machine learning model includes a CNN to employ convolutions and filters to classify each of the cell images. Other types of machine learning models may be implemented in other examples.

The computing device implementing the method 100 can include a display or other output device configured to provide a user-perceptible output (e.g., a graphical and/or textual representation) based on the method that is executed. The output can include a quantity (e.g., count) of cells according to their determined classification type or sub-type (e.g., determined at 106 and/or 110). The classification results, including from the Phase I and/or Phase II network, can also be included in an output to provide another quantitative or qualitative indication of disease state (e.g., SCD) based on the methods disclosed herein. In a further example, the method 100 and the classification at 106 and/or 110 to successive frames of a video, counting cells of specific types in each video frame. In this way, the behavior of individual cells could be tracked in a series of successive frames. For instance, an adhered cell may attach, stay in a given location for several frames, and then detach. The output, in this example, would be the number of frames that the cell has adhered, which would provide useful information about the adhesion strength under flow conditions for different cell types.

Thus, the method 100 implements deep learning models that may be implemented as part of an automated platform, which includes a microfluidic assay (e.g., the SCD BioChip) to quickly and consistently count sRBCs adhered to endothelial proteins (e.g., in a microfluidic device), and to classify the adhered cells into deformable and non-deformable types. Because the input consists of complex microscopy images of whole blood, the approach also can reliably disregard non-adhered sRBCs and other miscellaneous objects. As mentioned, while the method 100 has been described largely with respect to counting and classifying sRBCs, the method 100 is applicable to counting and classifying other objects. For example, the approach may be used, additionally or alternatively, for other metrics like white blood cell (WBC) content, WBC versus sRBC content, emergent sub-types and the like. Moreover, the systems and methods may be applied to classifying other biological objects in other contexts.

Figure 3:
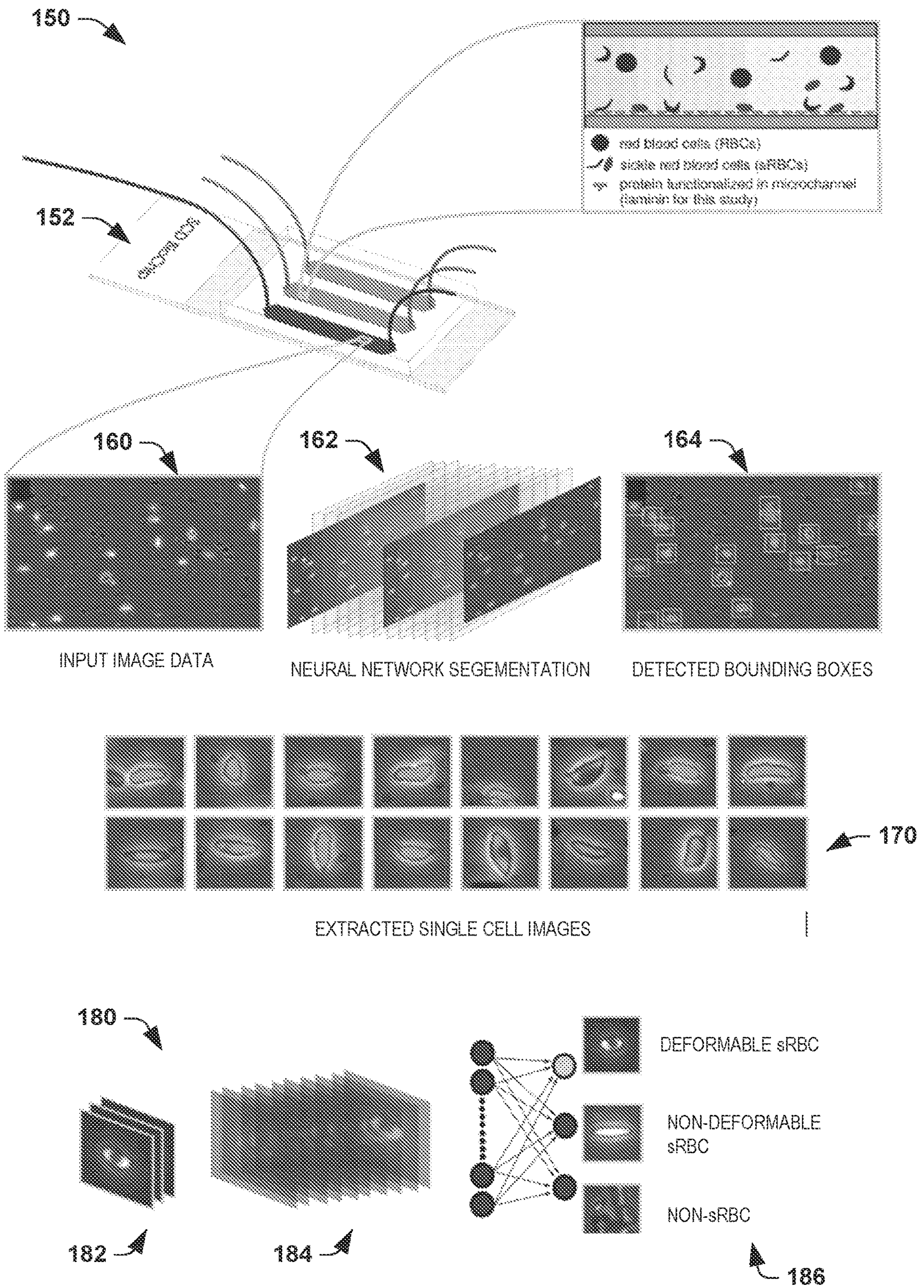
FIG. 3 depicts an example of an overall processing workflow pipeline for classifying objects.

FIG. 3 depicts an example of an overall architecture of a processing pipeline system 150 for classifying objects. The pipeline processing system 150 can be configured to implement the method 100 of FIG. 1. Accordingly, the description of FIG. 3 also refers to FIG. 1. The system 150 is configured to implement one or more neural network models trained for cell segmentation, detection and classification of objects represented in input image data 160. The input image data 160 can be acquired using an imaging modality, such as a digital microscope having a focal plane set to the protein-functionalized surface of a channel of a microfluidic device 152

In the example of FIG. 3, the system 150 includes two phases of analysis. Each phase of the system 150 can been built around a separately trained machine learning model. Because the system is used for image analysis of vast amounts of complex microscopy information contained in the input image data 160, which may contain numerous cellular objects under fluid flow, Phase 1 analysis is configured to perform segmentation and object detection of adhered sRBCs (e.g., corresponding to functions 104 and 106). Phase 2 analysis 180 is configured to implement further biophysical classification of sRBCs, such as into deformable and non-deformable types.

Phase 1 analysis includes a neural network 162 having an architecture configured to downsample and then upsample the input image data into a segmentation mask. The downsampling portion of the network constructs and learns feature vectors as input data for the upsampling part of the neural network, allowing it to find segmentation masks for the original input images. The system 150 may also crop and concatenate images similar to semantic segmentation networks.

As an example, given input image data 160 of a microchannel containing a blood sample, the network 162 learns to assign individual pixels to multiple object categories. In one example, the network 162 is trained to classify image objects or pixels into the following four categories: background, deformable adhered sRBC, non-deformable adhered sRBC, and non-functionally adhered/other (see, e.g., FIG. 8). The other category largely involves detached or freely flowing cells (e.g., cells not attached to endothelial proteins along the channel wall, as shown in FIG. 2E), which are easily distinguishable from adhered cells. In another example, the network 162 is trained to classify image pixels of a given input image to three categories: background, adhered sRBC, and non-functionally adhered/other (see, e.g., FIG. 9). The non-functionally adhered/other category largely, which effectively combines the latter two categories in the four-class pixel labeling scheme described above, involves detached or freely flowing cells (e.g., cells not attached to proteins along the channel wall, as shown in FIGS. 2E and 2F), which are easily distinguishable from adhered cells.

As an example, training of the network 162 may be performed using a cross-entropy loss function for penalizing wrong predictions of individual pixels. In another example, the network 162 can be trained a loss function that combines the cross-entropy loss $L_{CE}$ and Jaccard loss $L_{Jac}$. The $L_{CE}$ penalizes individual per-pixel segmentation, while the $L_{Jac}$ penalizes the network based on the intersection over the union between the predicted and ground truth segmentation mask. The latter is useful for training networks on segmentation tasks with imbalanced pixel classes.

The pixel labeling scheme (e.g., three- or four-class labeling scheme), which is used in examples of a Phase I segmentation network 162, is a first step toward capturing the complexity of features in the input image data 160. Ultimately, however, the pipeline is to classify entire objects rather than individual pixels. In some cases the network 162 might assign pixels from different classes to the same cell, such that there can be ambiguity in making definitive object classifications based on pixel labels (i.e., how to classify a cell with a comparable number of pixels assigned to the deformable and non-deformable sRBC classes). Accordingly in some examples, further refinement may be helpful, which provides motivation for including the Phase II network 180 in the system 150. In other examples, the classification and counting provided by the Phase I network 162 can provide satisfactory level of classification and the Phase II network 180 can be omitted from the system. Thus, the system 150 can rely on the Phase I network 162 to accurately identify clusters of pixels as adhered sRBCs. The system implements extraction function (e.g., at 108 of FIG. 1) to computes pixel bounding boxes around such clusters, shown at 170, in which each box is centered around the cluster centroid. The size of the box may be variable such as set based on the average size of the sRBCs in the channel images at the current magnification level magnification, so that one box typically contains an entire cell object. The boxes produced by the extraction function form a set of images, shown at 170, which are the input to the Phase II network.

As described herein, the Phase I network 162 can accurately identify clusters of pixels as adhered sRBCs. While, in some examples, the Phase I network 162 may not be as accurate in making the finer distinction between deformable and non-deformable adhered sRBCs, it can accurately identify clusters of pixels as adhered sRBCs. As shown at 164, an image processing algorithm (the extraction function) can compute bounding boxes around such clusters (e.g., boxes of 32×32 pixels or other sizes), in which each box is centered around the cluster centroid. The size of the box may be set based on an average size of the sRBCs in our channel images (e.g., at a given magnification level), so that each individual box may contain an entire cell. The bounding boxes are used for provide a set of extracted cell images, demonstrated at 170, which define the input 182 for the Phase II network 180.

As a further example, the extraction function, shown at 164, is programmed to extract the single-cell images 170 as follows. Starting with the example four-class segmentation mask generated at the end of Phase I, the pixels in these images are binarized according to the respective combined pixel classes by assigning 1 to sRBC pixels and 0 to non-sRBC pixels. Any small objects that form connected clusters of pixels, such as where the cluster size is smaller than a threshold number of (e.g., about 60) pixels, may be deleted. The threshold is set to enable removal clusters of debris from the images, while being small enough relative to the range of sRBC cell sizes to preserve clusters that are actually sRBCs. The threshold for discarding small clusters may be user-programmable and/or vary depending on image resolution. The centroids of the remaining clusters, ideally corresponding to sRBC cells, are computed and bounding boxes centered at each cluster centroid are determined for extracting the pixels therein, as shown at 170. Before the extracted cell images are input into the Phase II neural network for biophysical classification, each image may be resized according to the input layer of the Phase II neural network (e.g., from 32×32×3 to 224×224×3). Zero-centered normalization can also be applied.

In the Phase II neural network 180, the images 182 are run through a CNN 184 for biophysical classification. For example, the neural network 184 is programmed to perform a series of convolutions and filters, which ultimately classifies the image as a deformable sRBC, non-deformable sRBC or non-sRBC, as demonstrated at 186. For example, if the Phase I analysis was entirely error-free, there would be no input images (at 182) in Phase II corresponding to non-sRBC objects. But this category is included to filter out potential errors that could be made by the Phase I analysis 162, further enhancing the accuracy of the results through the application of Phase II. In an example, the structure of a Phase II classifier network 184 may be adapted from a deep learning, residual neural network, such as ResNet-50, such as may be pretrained on ImageNet.

In some examples where the input dataset 182 for Phase II may be considered a relatively small size dataset of manually classified cell images for training an image classification network, transfer learning may be implemented. Transfer learning can enhance training in cases with limited data. For example, the deep residual network called ResNet-50, pretrained on ImageNet, may work well in learning morphological features for our biophysical classification task. A k-fold cross-validation protocol may be conducted to estimate the accuracy of our machine learning model on test data.

Figure 4:
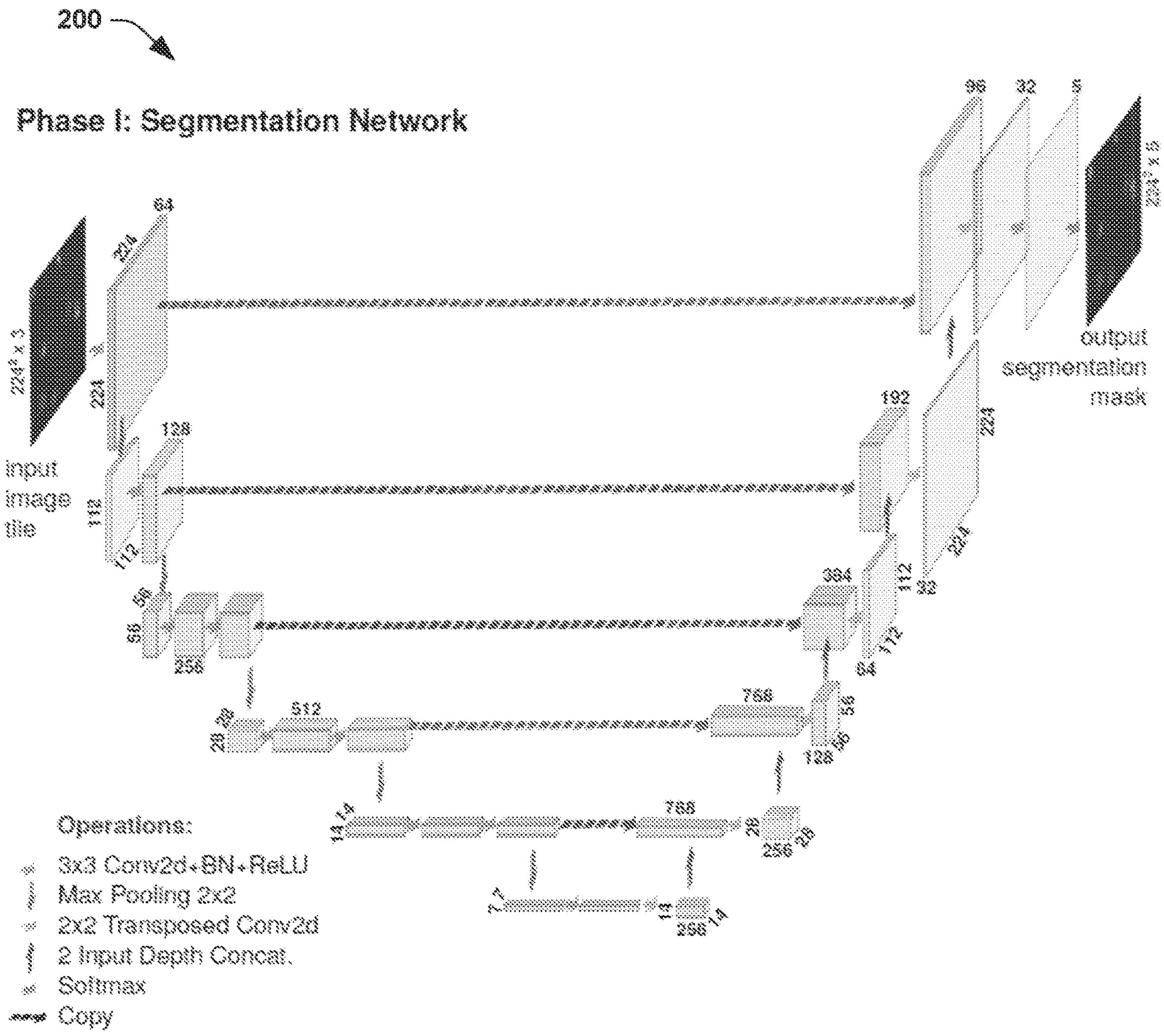
FIG. 4 depicts an example of an architecture for a convolutional neural network for semantic segmentation.

FIG. 4 depicts an example of an architecture for a CNN 200 that is configured semantic segmentation. The network 200 may be used as the first machine learning model at 104 in the method of FIG. 1 or as the Phase I network at 162 in FIG. 3. The network 200 implements five convolutional blocks that contain filters, nonlinear activation functions (ReLU), batch normalization, down (max), and up (transpose) sampling layers. Altogether, these layers sum to a total of 61 individual layers that take images as input and classify individual pixels into the four label categories to generate a segmentation mask (e.g., as generated at 104 or 162).

Before implementing the neural network 200 for segmentation and detection, the images may be preprocessed and prepared to provide the input image data. For example, the preprocessing may include stitching together of mosaic images of a single whole channel, which have been acquired by a microscope to provide a larger image with pixel dimensions that is an aggregate of the set of images. The raw whole channel image may be split into a plurality (e.g., about 1,000-4000) of equally-sized tiles by dividing the rectangular image with a number of vertical and horizontal partitions, leading to tiles with pixel dimensions (e.g., 150×150 or 300×262 pixels).

In an example, the network 200 has an input layer having a predetermined size in three-dimensions (e.g., 224×224×3 or 128×128×3), with the first two dimensions representing height and width in pixels, and the last dimension representing the number of channels. Though in some examples, tile images may be all grayscale, their format may vary depending on the experimental procedure for recording each image. For example, some images may have three channels and some just one channel. In the latter case, the first channel may be copied and then the copied channels concatenated two more times, creating images with three-channel depth. The width and height of the tile further may be resized to match the input size specifications of the network 200 (e.g., from 300×262×3 to 224×224×3 or from 150×150×3 to 128×128×3), such as by implementing a bicubic or other interpolation function, and apply zero-centered normalization.

For example, the network 200 is trained using supervised learning such that the data set is manually labeled (e.g., by a skilled user labeling objects in one of the respective classes). In an example, the labeling may be accomplished using the Image Labeler app that is implemented in Matlab R2019a. Other labeling computer software can be used in other examples. As described in this four-class example, each pixel may be assigned to one of four labels: background, deformable sRBC, non-deformable sRBC, and other (see, e.g., FIG. 8).

A common challenge in training semantic segmentation models, such as the network 200, is class imbalanced data. A class imbalance occurs when the frequency of occurrence of one or more classes characterizing the data set differs significantly in representation, usually by several orders of magnitude, from instances of the other classes. This problem can result in poor network performance in labeling the minority classes, a significant challenge for biomedical image segmentation in which frequently the minority class is the one under focus. A typical example of imbalance is in pathologies such as inflammatory tissues or cancer lesions, where the aberrant tissue patch or lesion is much smaller in size compared to the whole image. This issue leads to reduced capacity for learning features that correlate to the lesions. For the example of microchannel images, such as recorded from a microfluidic device, the background far outstrips the adhered sRBCs in representation, heavily skewing the data set. In the absence of balancing, since the cross-entropy loss sums over all the pixels in an image, it is possible that the network may misclassify adhered sRBC pixels, in some cases completely ignoring them. Because the accurately identifying the adhered cells, it is imperative to address this imbalance and improve accuracy for these minority classes.

In some examples, a transfer learning-oriented method may be used to overcome class imbalances within pixel-labeled training data. In place of a standard training procedure starting with starting weights drawn from a normal distribution, weights from a pre-trained network may be transferred into the network. The pre-training involves a more inherently class balanced data set, for example, 2,295 manually extracted images of deformable and non-deformable adhered sRBCs, as well as non-sRBC objects like out-of-focus cells. Unlike the set of 1,000 tiles described above, which typically contain multiple cells per tile, in this case we use single cell images, with bounding boxes of a predetermined size. Because the Phase I network architecture 200 has a fixed input layer size, we then resize these images to match the input specification (e.g., through bicubic interpolation). Examples for details of the two Phase I data sets (single-cell images and larger tiles) are summarized in the following Table.

| Phase | Dataset |
| --- | --- |
| I | Initial: 2,295 pixel-labeled single-cell images (each 32 × 32 pixels) Final: 1,000 pixel-labeled tiles (each 224 × 224 pixels) |
| II | 6,863 single-cell images (each 32 × 32 pixels) representing: 3,362 deformable sRBC, 1,449 non-deformable sRBC, 2,052 non-sRBC |

In the above example, the single cell images used in this pre-training had a much lower fraction of background pixels relative to the tiles. Thus, by pre-training the network on these images, the network may become biased to classify non-background pixels more accurately during the subsequent training on the tiles.

In another example, the Phase I network can be implemented as an encoder-decoder model that is programmed to implement convolutional blocks that contain filters, nonlinear activation functions (ReLU), batch normalization, down (max), and up (transpose) sampling layers. The final layer can be implemented as a softmax configured to predicts one hot encoded tensor, corresponding to one of the three classes: background, adhered sRBC, and non-functionally adhered/other. For our loss function, we choose to combine the binary cross-entropy $L_{CE}$ and Jaccard loss (i.e., intersection over union loss) $L_{Jac}$, expressed as:

$$\mathcal{L} = \mathcal{L}_{CE} + \mathcal{L}_{Jac},$$

$$\mathcal{L}_{CE} = -\frac{1}{N}\sum_{\alpha=1}^{N}\sum_{i=1}^{3}\left(p_i^{(\alpha)}\log\left(q_i^{(\alpha)}\right) + \left(1 - p_i^{(\alpha)}\right)\log\left(1 - q_i^{(\alpha)}\right)\right)$$

$$\mathcal{L}_{Jac} = -\log\left(\frac{\sum_{\alpha=1}^{N}\sum_{i=1}^{3} p_i^{(\alpha)} q_i^{(\alpha)}}{2N - \sum_{\alpha=1}^{N}\sum_{i=1}^{3} p_i^{(\alpha)} q_i^{(\alpha)}}\right) \equiv -\log(J).$$

Here N represents the number of data points in a batch to be analyzed, $p_i^{(\alpha)}$ the with component of the one hot encoded ground truth probability for the ath data point, and $q_i^{(\alpha)}$ the corresponding predicted softmax probability component. $L_{Jac}$ is the negative logarithm of the Jaccard index J, whose numerator is a measure of the size of the intersection between the ground truth segmentation mask and the predicted segmentation mask. The denominator is a measure of the size of the union between these two masks. Note that the 2N in the denominator represents the total size of the two masks (union plus intersection), so subtracting the intersection (the expression in the numerator) from 2N gives the size of the union. Furthermore, we compared our encoder-decoder segmentation model, which is tuned and optimized on our sRBC dataset, against the most recent state-of-the-art segmentation model called HR-net, which introduces novel connections between high-to-low resolutions in parallel during training. For both model architectures, the initialized weight parameters were sampled from a random normal distribution. As described below, however, the encoder-decoder analyzes images almost twice as fast as HR-net, and hence was our preferred segmentation approach. An example of the Phase I network architectures is set forth in https://github.com/hincz-lab/DeepLearning-SCDBiochip.

As described with respect to 106 of FIG. 1, the input images for the Phase II network 184 are extracted based on the segmentation mask (from and bounding boxes centered on respective cells) to provide cell images, such as each including a single cell. For classifying sRBCs, the segmentation mask can be implemented as a three- or four-class mask. Ideally, the cells in the input images are all adhered sRBCs, but there may be a small subset of non-sRBC objects, a source of error that the Phase II classifier network can be configured to mitigate.

Figure 5:
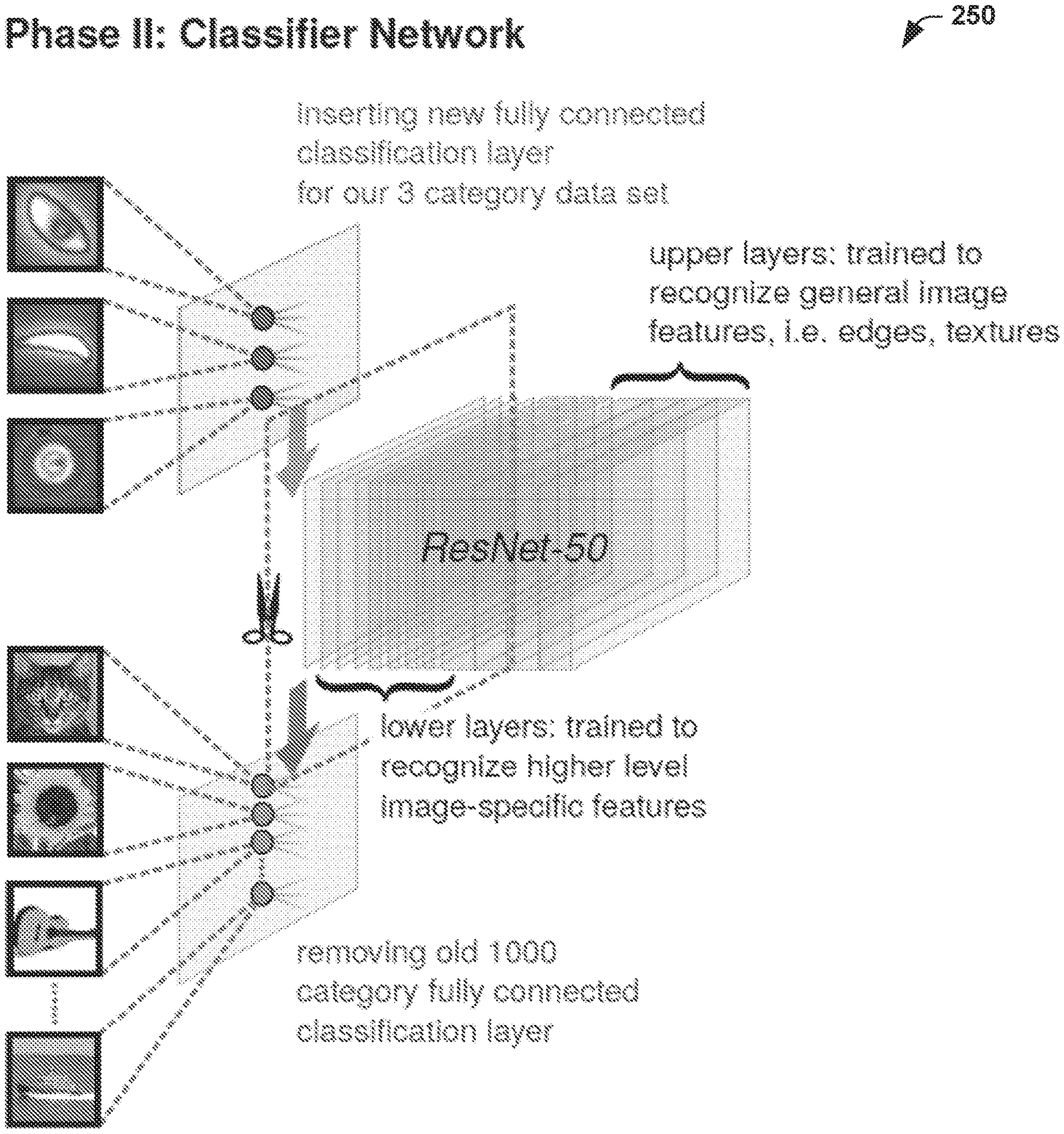
FIG. 5 depicts an example of a transfer learning workflow that may be used for training a convolutional neural network for object classification.

FIG. 5 depicts an example of a transfer learning workflow that may be used for training a CNN for object classification, such as corresponding to the Phase II classifier network implemented at 106 (FIG. 1) and 184 (FIG. 3). In an example, the structure of a Phase II cell classifier network 184 may be adapted from ResNet-50, which is a very deep residual neural network. Residual neural networks implement skip connections in the hopes of avoiding vanishing gradients. The Phase II cell classifier network may be pre-trained on the reduced ImageNet ILSVRC database, consisting of over 1 million training images and belonging to 1000 different classes.

Figure 11A:
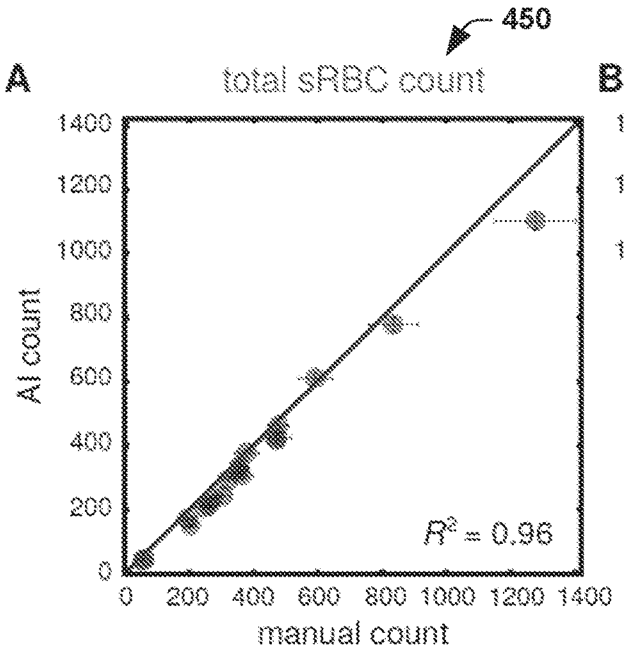
FIGS. 11A, 11B and 11C are graphs depicting a comparison of performance between counts determined by manual counting and by machine learning approach disclosed herein.
Figure 11B:
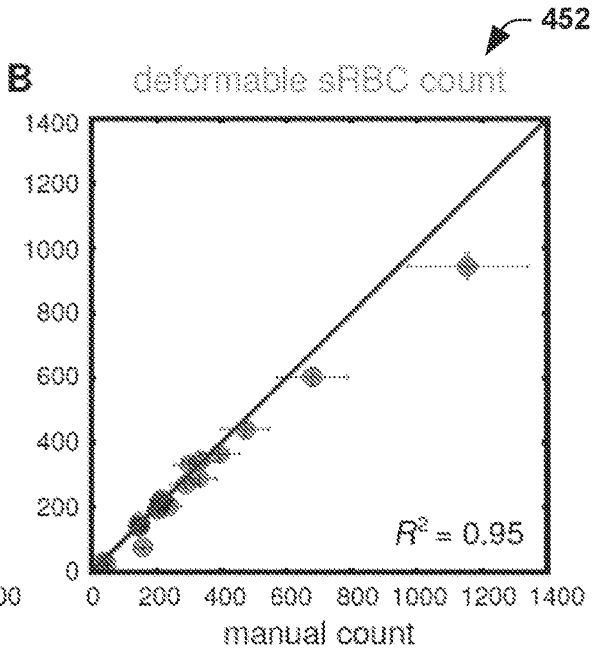
Figure 11C:
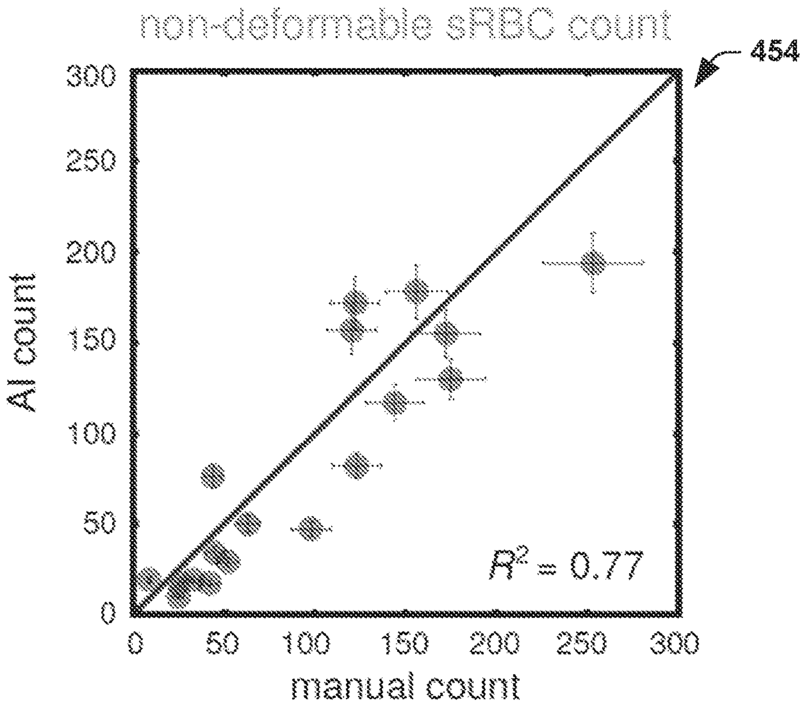

As one example, the training set for supervised learning in Phase II consists of 6,863 single-cell images in three object categories: deformable sRBC (3,362 images), non-deformable sRBC (1,449 images), and non-sRBC (2,052 images). Examples of these images are shown FIG. 11. In terms of curating the training data set, a batch of individual objects were manually extracted from a large set of channel images displaying different luminescence and granularity features that covered the broad spectrum of sample and experimental variance (see FIG. 2A). However, after completing the Phase I network, the data set was expanded to include the single-cell images generated by Phase I, though the labels were manually verified to correct any errors. The data set also covers different physiological conditions like normoxia and hypoxia, which allows the resulting image processing pipeline (FIG. 3) to handle data from a wide range of SCD assays.

The overall data set size may be relatively small for the complex classification task, which requires learning subtle morphological features in cells of various sizes, shapes, and orientations. Accordingly, a transfer learning framework: rather than initializing the network with randomly chosen weights, we start with weights pre-trained on ImageNet, which allows a higher starting accuracy on the starting data set, faster convergence, and better asymptotic accuracy. To tailor the network for the sRBC classification the final fully-connected layer of ResNet-50, which has output size 1000, was replaced by a layer with three output neurons corresponding to the three object classes, as shown in FIG. 5.

As a further example, the data set was split randomly into 80% training and 20% testing subsets, and the network was trained with maximum epoch number 10 and mini-batch size 64. Each training session had 850 iterations, and thus 85 iterations per epoch. This process took approximately 13 minutes per fold on an NVIDIA GeForce RTX 2080Ti GPU. To prevent overfitting, data augmentation was implemented on the training subset. The augmentation included implementing random reflections along the horizon and vertical symmetry lines (e.g., an image was reflected with a probability of 50% during each iteration). The data augmentation may also include x and y translations, where the translation distance (in pixels) is picked randomly from a uniform distribution within a chosen interval: [10, 10]. Lastly, the images were augmented with random rotations of small angles between the values −5 and 5 degrees.

Example Results—Performance and Validation

Figure 6:
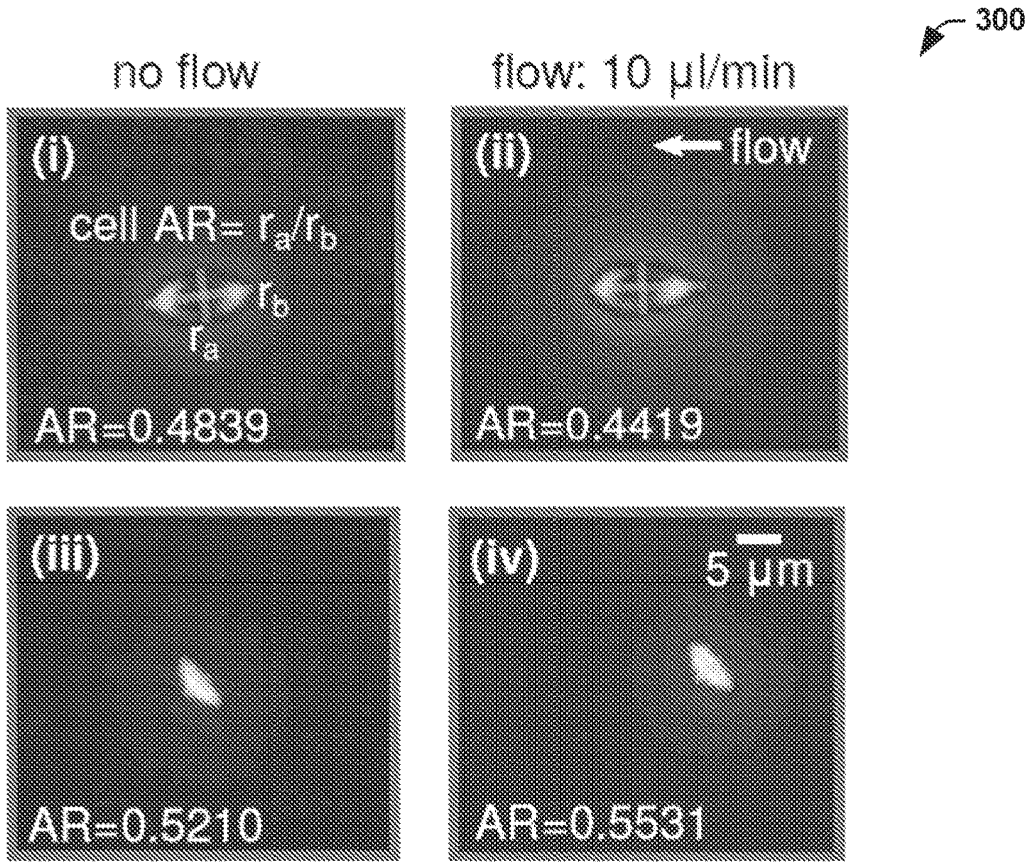
FIG. 6 depicts examples of cell aspect ratios for cells under flow and no flow conditions.
Figure 7:
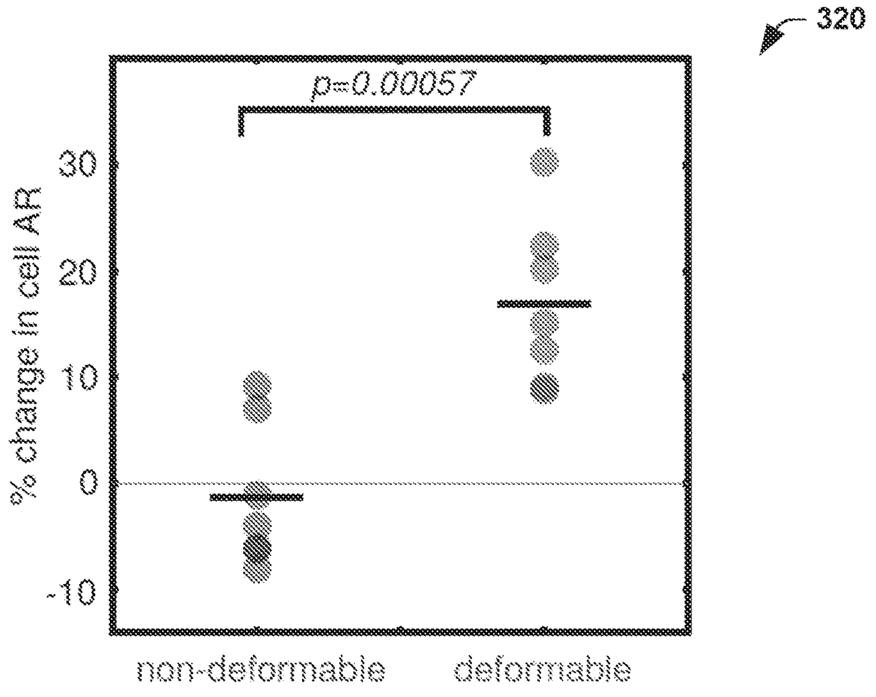
FIG. 7 is a graph comparing the change in aspect ratio for cells having different deformability characteristics.

To validate the connection between adhered sRBC morphology and deformability in our experimental setup, pairs of images of the microfluidic channel were analyzed first under flow (10 μL/min) and then under no flow conditions. These images were examined to look for sRBCs that had not detached or moved significantly between the two image captures, to allow for legitimate comparison. As shown in the images 300 of FIG. 6, a relative change in cell aspect ratio (AR) under the two flow conditions may be analyzed for each cell to provide a measure of cellular deformability. The cellular AR may be defined as the ratio of the estimated minor to the major axis for a given cell. A set of 14 cells was identified and manually classified as seven deformable and seven non-deformable according to the morphological characteristics (see, e.g., FIG. 2). After analyzing the cellular AR of the adhered RBCs under the two flow conditions, it was determined that the morphology of the sRBCs correlates to the deformability characteristics. The cells classified morphologically as deformable showed a mean change in AR of about 20% on average between flow and no flow conditions. For those classified as non-deformable sRBCs, the average percent change in AR was close to zero. Results are summarized in FIG. 7. Given the heterogeneity of the cell shapes and errors introduced by the pixelation of the images, the AR changes of each subtype have a distribution, but the difference in the average AR between the two distributions is statistically significant (p=0.00057). These results reproduce the link between morphology and deformability observed in Alapan et al. (Alapan Y, Little J, Gurkan U. *Heterogeneous red blood cell adhesion and deformability in sickle cell disease*. Sci Rep. 2014; 4(7173):1-8). Thus, the classification into subtypes produced by the algorithm should be strongly correlated with a key biophysical properties of the individual sRBCs.

Figure 8:
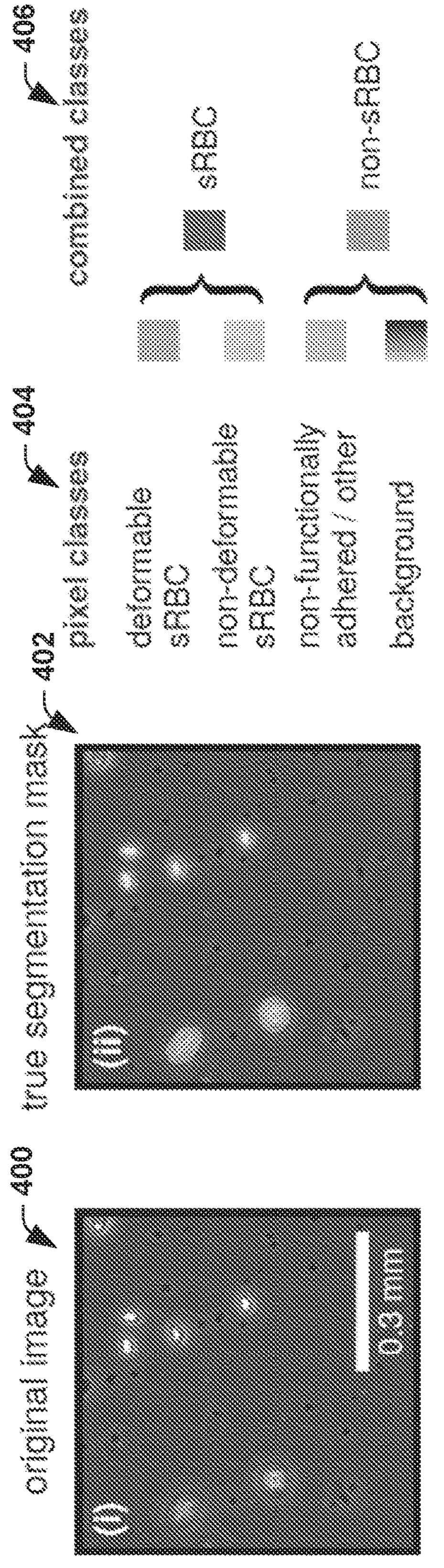
FIG. 8 depicts an image tile and associated segmentation mask for different pixels classes for an example Phase I network.

FIG. 8 depicts examples of an original image tile 400 and its labeled counterpart (segmentation mask) 402 that can be produced by a Phase I network 164. In this example, the network is trained to produce a four-class segmentation mask 402 for identify four respective pixel classes 404, including deformable adhered sRBC, non-deformable adhered sRBC, non-functionally adhered/other and background.

Figure 9:
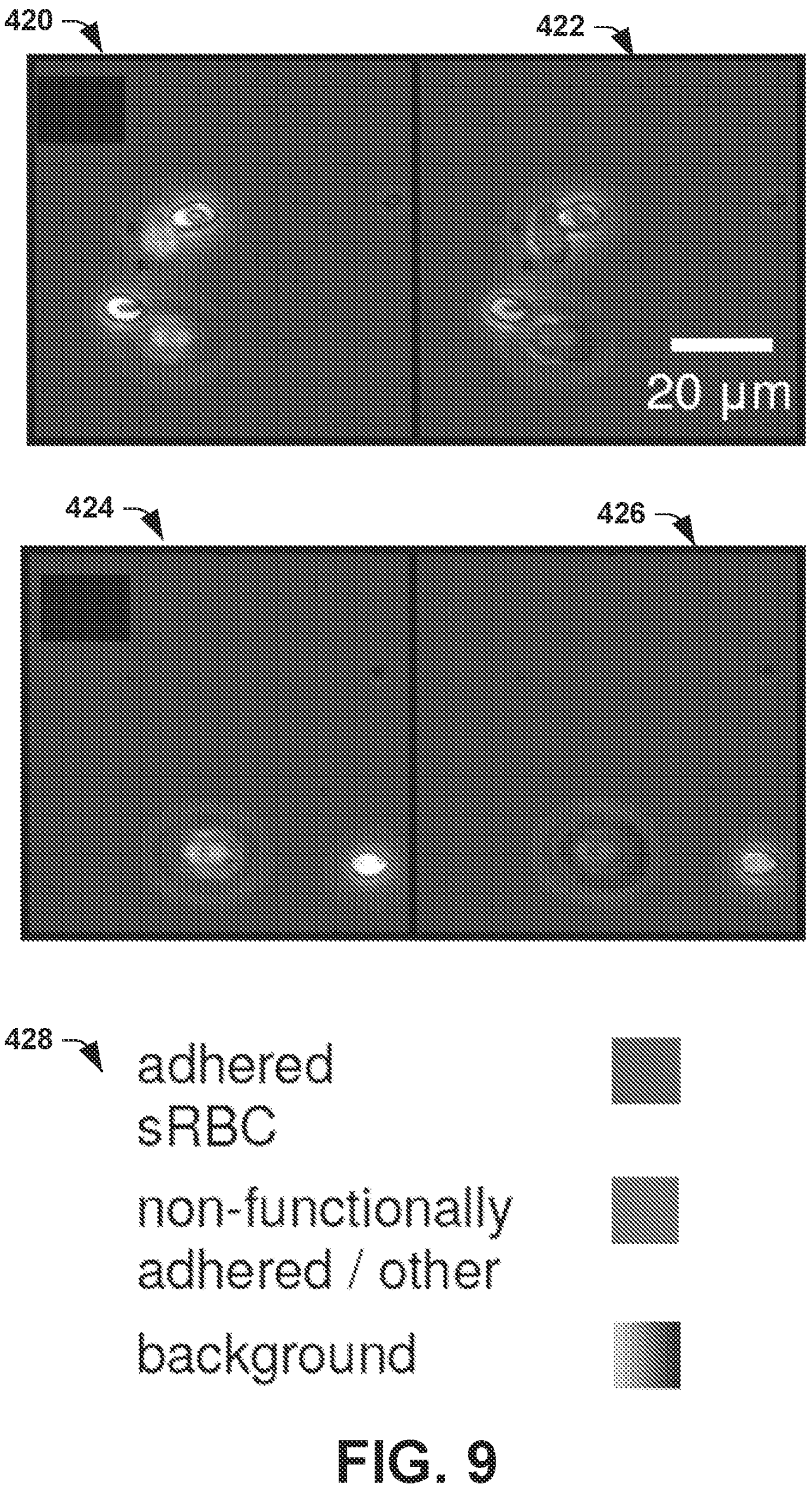
FIG. 9 depicts another example of an image tile and associated segmentation mask for different pixels classes for another example Phase I network.

FIG. 9 depicts an example of image tiles and segmentation masks that can be produced by a Phase I network 164. In particular, FIG. 9 includes an original image tile 420 and a segmentation mask 422 showing deformable sRBCs and -functionally adhered/other objects. FIG. 9 also shows tile 424 with non-deformable sRBCs and other objects along with a corresponding segmentation mask 426 that can be generated by the Phase I network. In this example, the network is trained to produce a three-class segmentation masks 402 for identifying three respective pixel classes 448, adhered sRBC, non-functionally adhered/other and background.

Phase I Network Performance

Figure 10:
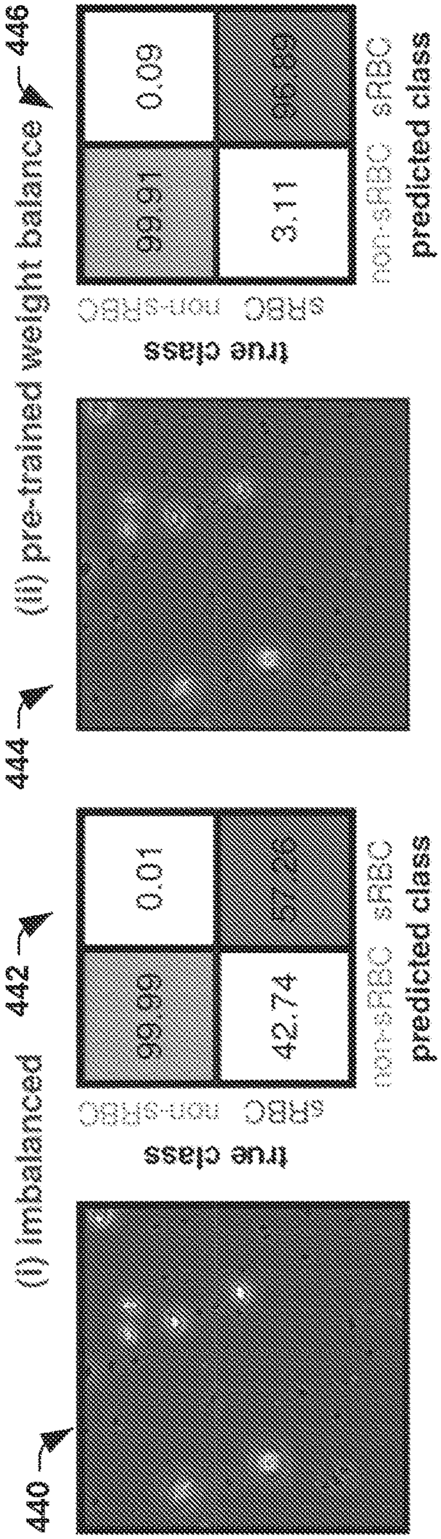
FIG. 10 depicts an example of segmentation masks and confusion matrices derived from an image tile by a Phase I network trained with balance control and trained without balance control.

To test the efficacy of the approach described herein for mitigating class imbalance in Phase I, the performance of the Phase I network (pre-trained on class-balanced images) was compared against one trained without any kind of balance control. Confusion matrix results for each network are shown in FIG. 10, along with sample segmentation masks generated by the two networks. Since the main utility of the Phase I network is to distinguish sRBC from non-sRBC pixels, the confusion matrices are presented in terms of these two combined classes. Unsurprisingly, the imbalanced network performed poorly for the minority (sRBC) class, while the Phase I network described herein worked very well for both classes. The Phase I network described herein begins to outperform the imbalanced one on both the training and validation subsets early in the process, and achieves smaller losses at the end of the training. Other metrics could be used to evaluate network performance.

Segmentation Performance Evaluation

Figure 12:
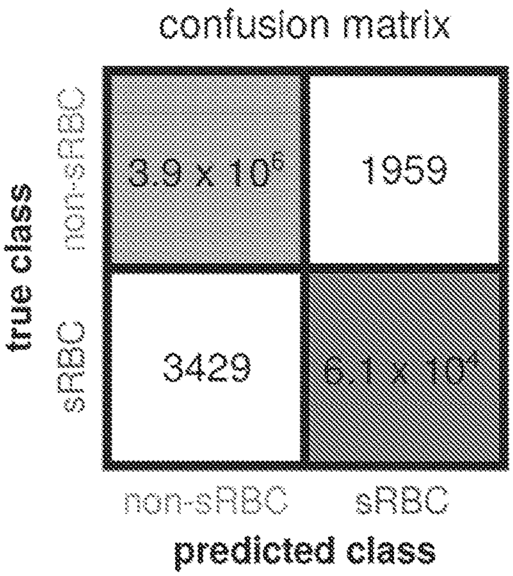
FIG. 12 depicts a confusion matrix for pixel label count.
Figure 13:
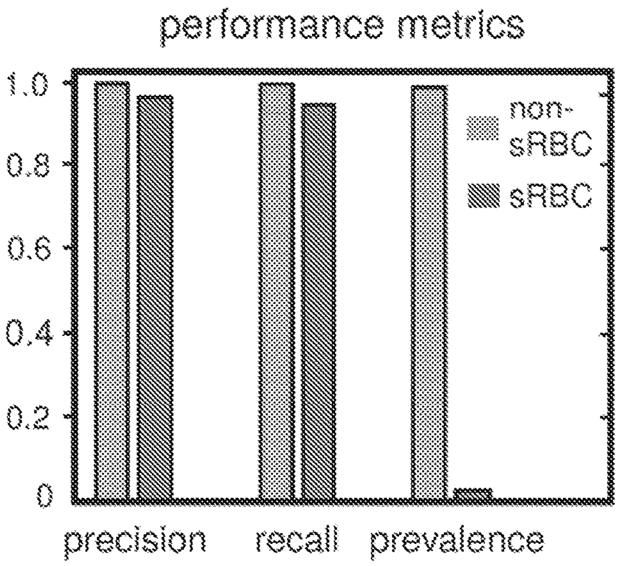
FIG. 13 is a graph depicting performance of an example Phase I network.

To quantify overall performance of the Phase I network, the performance metrics defined below were computed for a given class i, where i corresponds to either non-sRBC or Here TPi, TNi, FPi, and FNi denote the number of true positive, true negative, false positive and false negative outcomes in classifying a given target pixel into class i. "Total" represents the total number of pixels involved in the evaluation. Precision indicates the agreement between predicted and target class labels, while recall measures the effectiveness of the neural network's classification ability when identifying pixel-classes. Prevalence indicates how often a specific class actually occurs in the data set. The results are summarized in FIGS. 12 and 13. FIG. 12 depicts a confusion matrix for pixel label count. FIG. 13 is a graph depicting performance of a Phase I network, including for precision, recall and prevalence. The Phase I network can achieve state-of-the-art accuracy in segmentation of channel images from whole blood compared to similar studies.

From FIGS. 12 and 13, it is shown that despite the huge imbalance in non-sRBC vs. sRBC pixels (evident in the pixel count confusion matrix of FIG. 12 and the discrepancy in prevalence of FIG. 13), the Phase I network, as described herein is successful. That is, the Phase I network is able to reach state-of-the-art accuracy in segmentation of channel images from whole blood experiments compared to similar studies in literature, for example, reaching ~97% accuracy in non-sRBC/sRBC pixel distinction in the testing set. Error arising from segmentation of cell boundaries rather than the cell itself do not significantly affect the final results in the multi-phase pipeline system 150 (FIG. 3).

Phase II Network Performance

To quantify overall performance of our Phase II network, performance metrics, shown below can be computed for a given class i, where i corresponds to either deformable sRBC, non-deformable sRBC, or non-sRBC cell:

$$\text{Precision}(i) = \frac{TP_i}{TP_i + FP_i},$$

$$\text{Recall}(i) = \frac{TP_i}{TP_i + FN_i},$$

$$\text{Accuracy}(i) = \frac{TP_i + TN_i}{\text{Total}},$$

Here $TP_i$, $TN_i$, $FP_i$, and $FN_i$ denote the number of true positive, true negative, false positive and 435 false negative outcomes in classifying a given cell image into class i. "Total" represents the total 436 number of images involved in the evaluation. Precision indicates the agreement between predicted and target class labels, while recall measures the effectiveness of the neural network's classification ability when identifying cell classes.

Figure 14:
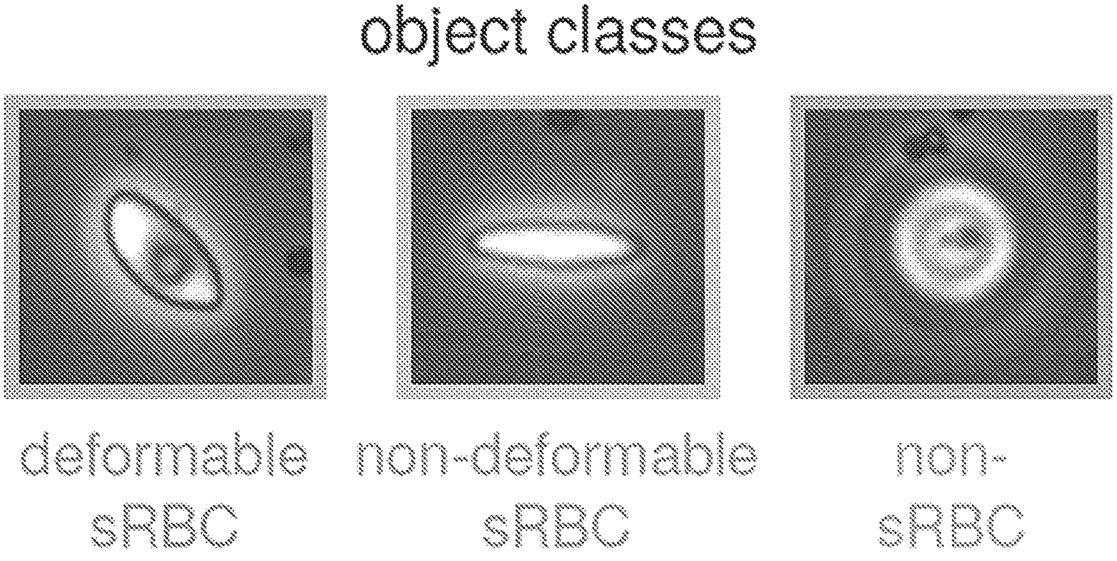
FIG. 14 depicts example of single cell images of different classifier categories.

During learning, the network weights are optimized to make the class predictions for the training data set as accurate as possible. However, depending on the training set and the stochastic nature of the optimization process, the accuracy of the network on the testing set can vary. Attention to this issue becomes imperative when dealing with smaller data sets for classification tasks, like in our Phase II case. k-fold cross-validation is one approach to validate the overall performance of the network in this scenario. The general procedure starts by shuffling the total data set before splitting it into training/validation subsets, to generate an ensemble of k such unique subsets (or folds). In an example, we choose k=5, with an 80/20% split for training/validation sets. Each fold consists of a unique combination of 20% of the images as the hold-out (validation) set, and the remaining 80% as the training set. Our combined data set of 6863 total images thus generates five unique folds with training and validation sets containing 5488 and 1372 images each (accounting for rounding off). Finally, we fit the neural network parameters on the training set and evaluate the performance on the validation set for five unique runs. Then for each single run, we collect the training and validation accuracy. We also show the mean and standard deviation of all the folds, with the small standard deviation being an indicator that our training did not suffer from overfitting. FIG. 14 shows example Phase II input images for each classifier category.

Figure 15B:
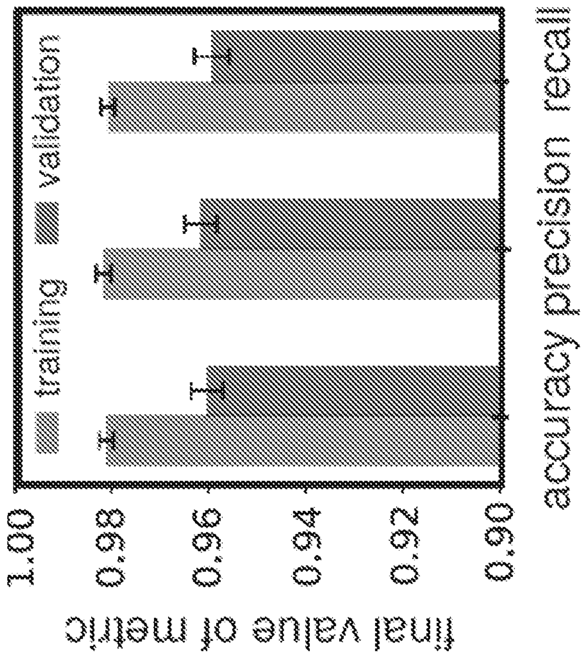
FIGS. 15A and 15B depicts examples of training history and performance metrics of an example Phase II network.
Figure 15A:
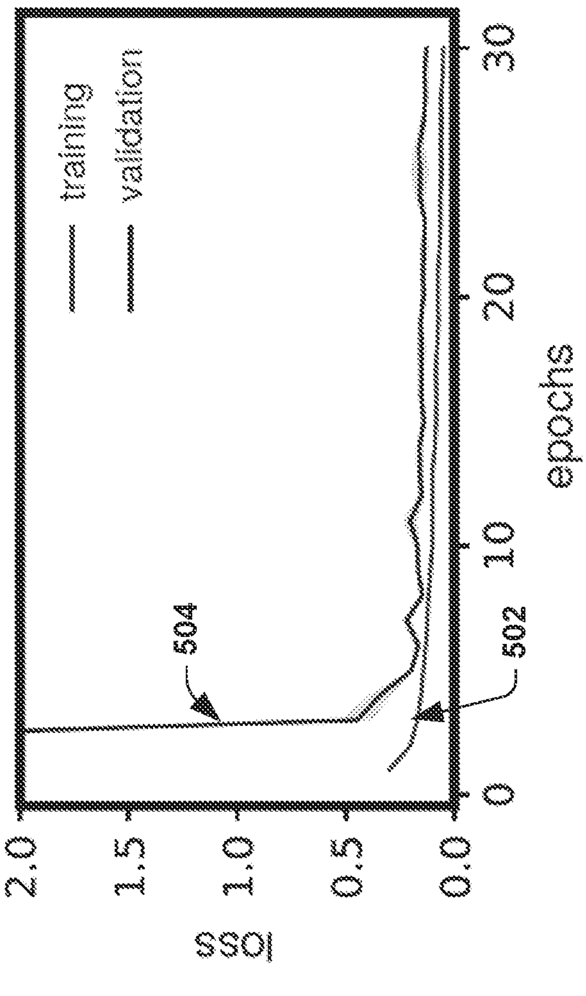

FIG. 15A shows an example graph of training and validation history of the loss function for the Phase II network. Training history is shown at 502 and validation is shown at 504. FIG. 15A shows metrics highlighting the typical performance, which averaged to 0.960±0.003 accuracy, 0.962±0.003 precision, and 0.959±0.004 recall in object classification over the folds. Furthermore, in terms of loss, accuracy, precision and recall during training, our fine-tuned ResNet-50 model outperforms the vanilla and fine-tuned Xception model variants on the validation set, averaged over the k-fold sets. FIG. 15B is a graph showing performance metric values for both training and validation reached by the Phase II network at the end of training over 30 epochs. Uncertainties indicate spread around the mean of each metric over the 5 folds.

The systems and methods disclosed herein can be implemented as a clinical tool for analyzing cells, such as blood cells, and other cellular objects within a microfluidic SCD adhesion assay. The systems and methods disclosed herein reduce the need for expert user input, enabling the processing of large amounts of image data with highly accurate results. For example, the systems and methods disclosed herein can identify sRBCs and other objects in complex, whole channel bright field images, and distinguish between their morphological subtypes (deformable and non-deformable). These subtypes are in turn strongly correlated with sRBC biomechanical properties, making the image analysis method a fast, high throughput proxy for the much more laborious cell-by-cell direct measurement of membrane biophysical properties of the cells, including deformability. While many examples disclosed herein are directed to classifying deformable and non-deformable sRBCs, the systems and methods disclosed herein are applicable to classifying other cells and objects, such as including sRBC sub-types, white blood cell (WBC) content, WBC versus sRBC content, emergent sub-types and the like.

In further view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processors of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a,", "an," "a first," or "another" element, or the equivalent thereof, it should be interpreted to include one or more than one such element, neither requiring nor excluding two or more such elements. As used herein, the term "based on" means based at least in part on.

What is claimed is:

1. A computer-implemented method comprising:

storing image data that includes an input image of a blood sample within a blood monitoring device, wherein the blood monitoring device comprises a microfluidic device that includes a microchannel configured to emulate blood vessels in vivo, the input image includes the blood sample within the microchannel, and the microchannel includes a functionalized adhesion region that is adapted to adhere to blood cells of interest within the blood sample, and the image is acquired while the blood sample is flowing through the microchannel;

generating, by a first machine learning model, a segmentation mask that assigns pixels in the input image to one of a plurality of classes, wherein the plurality of classes correlate to respective known biophysical properties of blood cells, and the first machine learning model is trained to detect red blood cells and/or subtypes of red blood cells;

extracting cell images from the input image based on the segmentation mask, in which each extracted cell image includes a respective cluster of the pixels assigned to the one of the plurality of classes; and classifying, by a second machine learning model, each of the extracted cell images to specify morphological subtypes of the red blood cells and/or the subtypes of red blood cells detected by the first machine learning model, wherein the second machine learning model is trained to distinguish subtypes of red blood cells based on morphology.

2. The method of claim 1, wherein the second machine learning model comprises a convolutional neural network to employ convolutions and filters to classify each of the extracted cell images.

3. The method of claim 1, wherein the extracting further comprises:

clustering the pixels in the segmentation mask to define respective pixel clusters according to the assigned class to detect red blood cells in the input image;

identifying centroids for each respective pixel cluster; and detecting bounding boxes around each of the identified centroids, wherein each cell image is generated based on pixels within the detected bounding box.

4. The method of claim 3, wherein the first machine learning model comprises a first convolutional neural network to classify pixels in the image according to a respective class of sickle red blood cells (sRBCs) thereof and to generate the segmentation mask to include cell objects segmented from clusters of pixels based on the assigned class of the pixels.

5. The method of claim 4, wherein the first convolutional neural network is configured to downsample the input image to generate feature vectors and to upsample the input image based on the feature vectors to generate the segmentation mask.

6. The method of claim 1, further comprising computing a count for a number of red blood cells and/or subtypes thereof detected by the first machine learning model.

7. The method of claim 1, wherein the plurality of classes include at least two of background, deformable adhered sickle red blood cell (sRBC), non-deformable adhered sRBC, and non-functionally adhered/other deformable sRBC.

8. The method of claim 1, wherein at least some of the known biophysical properties of blood cells relate to an adhesive property of blood cells within the adhesion region, and wherein the subtype of red blood cell includes a combined class of adhered sickle red blood cells (sRBCs), and wherein the second machine learning model is configured to classify the red blood cells, based on morphology, into deformable and non-deformable subtypes of sRBCs.

9. The method of claim 8, wherein the image data includes a series of successive frames of video images, and the method further comprises tracking a behavior of respective red blood cells in the series of successive frames and providing an output indicative of the adhesive property of the respective red blood cells.

10. One or more non-transitory machine readable media having instructions, which when executed by a processor perform the method of claim 1.

11. A system comprising:

a microfluidic device configured to contain a blood sample, the microfluidic device comprising a channel configured to emulate blood vessels in vivo, wherein the channel comprises at least one functionalized adhesion region adapted to adhere to blood cells of interest within the blood sample;

a processor; and one or more non-transitory machine readable media to store instructions and data, the data including an input image of the blood sample within the channel, the processor configured to access the media and execute the instructions comprising:

a first machine learning model trained to detect red blood cells and/or subtypes of red blood cells and generate a segmentation mask that assigns pixels in the input image to one of a plurality of classes that correlate to respective known biophysical properties of red blood cells;

extraction code programmed to extract cell images from the input image based on the segmentation mask, in which each extracted cell image includes a respective cluster of the pixels assigned to a respective one of the plurality of classes; and a second machine learning model trained to classify the extracted cell images to specify morphological subtypes for the red blood cells and/or the subtypes of red blood cells detected by the first machine learning model.

12. The system of claim 11, wherein the plurality of classes include at least two of background, deformable adhered sickle red blood cell (sRBC), non-deformable adhered sRBC, and non-functionally adhered/other deformable sRBC.

13. The system of claim 11, wherein the first machine learning model comprises a first convolutional neural network to classify pixels in the input image according to a respective class of sickle red blood cells (sRBCs) thereof and to generate the segmentation mask to include cell objects segmented from clusters of pixels based on the assigned class of the pixels.

14. The system of claim 13, wherein the second machine learning model comprises a second convolutional neural network to employ convolutions and filters to classify each of the extracted cell images.

15. The system of claim 13, wherein the first convolutional neural network is programmed to downsample the input image to generate feature vectors and to upsample the input image based on the feature vectors to generate the segmentation mask.

16. The system of claim 11, further comprising program code programmed to compute a count for a number of cells having the given type of blood cell detected by the first machine learning model.

17. The system of claim 11, wherein at least some of the known biophysical properties of blood cells relate to an adhesive property of blood cells within the adhesion region, and wherein the subtype of red blood cell includes a combined class of adhered sickle red blood cells (sRBCs), and wherein the second machine learning model is configured to classify the red blood cells, based on morphology, into deformable and non-deformable subtypes of sRBCs.

18. The system of claim 17, wherein the input image includes a series of successive frames of video images, and the instructions further comprise code programmed to track a behavior of respective cells in the series of successive frames and provide an output indicative of the adhesive property of the respective red blood cells.

19. The system of claim 11, wherein the input image is acquired while the blood is flowing through the channel of the microfluidic device.

20. The system of claim 11 wherein the input image is acquired while the blood is not flowing through the microfluidic device.

21. A system comprising:

a microfluidic device configured to contain a blood sample, the microfluidic device comprising a channel configured to emulate blood vessels in vivo;

a processor; and one or more non-transitory machine readable media to store instructions and data, the data including an input image of the blood sample within the channel, the processor configured to access the media and execute the instructions comprising:

a first machine learning model trained to detect red blood cells and/or subtypes of red blood cells and generate a segmentation mask that assigns pixels in the input image to one of a plurality of classes that correlate to respective known biophysical properties of red blood cells;

extraction code programmed to extract cell images from the input image based on the segmentation mask, in which each extracted cell image includes a respective cluster of the pixels assigned to a respective one of the plurality of classes; and a second machine learning model trained to classify the extracted cell images to specify morphological subtypes for the red blood cells and/or the subtypes of red blood cells detected by the first machine learning model, wherein the extraction code is further programmed to:

cluster the pixels in the segmentation mask to define respective pixel clusters according to the assigned class to detect cell objects in the input image;

identify centroids for each respective pixel cluster; and detect bounding boxes around each of the identified centroids, wherein each extracted cell image is generated based on pixels within the detected bounding box.

* * * * *